United States Patent [19]

Gupta

[11] Patent Number: 4,694,111

[45] Date of Patent: Sep. 15, 1987

[54] ALKOXYALKYLATION OF PHENOL

[75] Inventor: Balaram B. G. Gupta, North Plainfield, N.J.

[73] Assignee: Celanese Corporation, New York, N.Y.

[21] Appl. No.: 883,675

[22] Filed: Jul. 9, 1986

[51] Int. Cl.$^4$ ............................................. C07C 41/01
[52] U.S. Cl. .................................. 568/662; 568/626; 568/322; 568/727
[58] Field of Search ................................ 568/727, 662

[56] References Cited

U.S. PATENT DOCUMENTS 3,728,408  4/1973  Tobias ................................. 568/727

Primary Examiner—Howard T. Mars
Attorney, Agent, or Firm—Marvin Turken

[57] ABSTRACT

The production of a 1-hydroxy-2-lower alkoxyalkyl benzene, e.g. 2-(1'-methoxyethyl) phenol, is carried out by reacting phenol with a lower acetal or ketal, e.g., 1,1-dimethoxyethane at an elevated temperature in the presence of an H-ZSM-5 zeolite, as catalyst.

16 Claims, No Drawings

ALKOXYALKYLATION OF PHENOL

This invention relates to a process for producing 1-hydroxy-2-lower alkoxyalkyl benzenes such as 2-(1'-methoxyethyl) phenol.

BACKGROUND OF THE INVENTION

Compounds such as 1-hydroxy-2-lower alkoxyalkyl benzenes, e.g. 2-(1'-methoxyethyl) phenol, have a variety of different end uses. Thus, 2-(1'-alkoxyalkyl) phenols such as 2-(1'-methoxyethyl) phenol may be employed as antioxidants in polymer compositions. Furthermore, 1'-hydroxy-2-(1'-lower alkoxyethyl) benzenes such as 2-(1-methoxyethyl) phenol may be dealkoxylated by means well-known in the art to the corresponding vinyl compound, e.g. 2-vinylphenol, which may be polymerized into polymers having various applications, e.g. in photoresist or metal treatment compositions.

Various zeolites and zeolites-type materials are known in the art for the catalysis of chemical reactions. For example, U.S. Pat. No. 3,702,886, of Argauer, discloses a class of synthetic zeolites, characterized as "Zeolite ZSM-5", which are effective for the catalysis of various hydrocarbon conversion processes.

U.S. Pat. No. 4,371,714 of Young discloses a process for the alkylation of phenol or its alkyl ethers in the presence of a particular type of zeolite catalyst, e.g. ZSM-5, to produce a product rich in 4-alkyl phenyl alkyl ethers.

Applicant's pending application Ser. No. 803,194, filed Dec. 2, 1985, teaches the use of ZSM-5 zeolites as catalysts for the reaction of phenol and a lower alkanoic acid, e.g. acetic acid, to form 2-hydroxyphenyl lower alkyl ketone such as 2-hydroxyacetophenone.

Applicant's pending application Ser. No. 844,641 filed Mar. 27, 1986 teaches the reaction of a lower alkyl- or phenyl substituted benzene, e.g., toluene, ethylbenzene or biphenyl, with a lower alkanoic acid, e.g., acetic acid, in the presence of a medium-pore, pentasil-type molecular sieve, e.g. a ZSM-5 zeolite, to produce a 4-lower alkyl- or 4-phenyl ring-substituted phenyl lower ketone, e.g., 4-methylacetophenone, 4-ethylacetophenone, or 4-phenylacetophenone.

SUMMARY OF THE INVENTION

In accordance with this invention, phenol is reacted with a lower acetal or ketal, e.g., 1,1-dimethoxyethane, in the presence of a protonated, i.e. hydrogen form of a ZSM-5 zeolite catalyst, to produce a 1-hydroxy-2-lower alkoxyalkyl benzene such as 2-(1'-methoxyethyl) phenol. The protonated ZSM-5 zeolite may be referred to as an H-ZSM-5 zeolite. Surprisingly, it has been found that of the three possible isomers of hydroxy-lower alkoxyalkyl benzene which could theoretically result from the foregoing process, only the 1,2-isomer is produced in significant amount.

DESCRIPTION OF SPECIFIC EMBODIMENTS

The reaction between phenol and the lower acetal or ketal proceeds in accordance with the following equation:

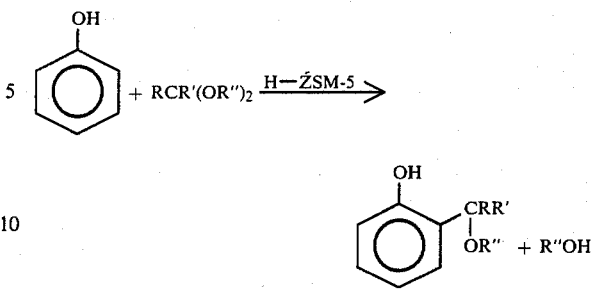

where, R and R' are each hydrogen or lower alkyl, e.g. containing 1 to 3 carbon atoms, and R" is lower alkyl, e.g. containing 1 to 3 carbon atoms. If R, R', and R" are lower alkyl, they may be the same or different and may separately be, for example, methyl, ethyl, n-propyl or isopropyl.

If the lower acetal or ketal is 1,1-dimethoxy ethane, i.e., R and R" are methyl and R' is hydrogen, the reaction proceeds as in the following equation:

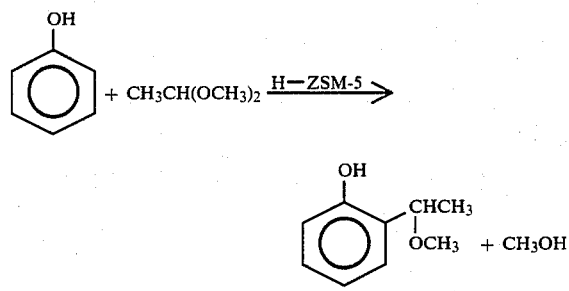

The H-ZSM-5-zeolites contemplated as catalysts under this invention are prepared by replacing with hydrogen ions most of the cations of a ZSM-5 zeolite, the composition, characteristics and preparation of which are set out in the previously cited U.S. Pat. No. 3,702,886 of Argauer, the entire disclosure of which is incorporated by reference. These ZSM-5 zeolites have the following formula:

$$0.9 \pm 0.2 M_{2/n}O : W_2O_3 : 5\text{-}100 YO_2 : zH_2O$$

wherein M is a cation, n is the valence of said cation, W is selected from the group consisting of aluminum and gallium, Y is selected from the group consisting of silicon and germanium, and z is from 0 to 40. In a preferred synthesized form, the zeolite has a formula, in terms of mole ratios of oxides, as follows:

$$0.9 \pm 0.2 M_{2/n}O : Al_2O_3 : 5\text{-}100 SiO_2 : zH_2O$$

and M is selected from the group consisting of a mixture of alkali metal cations, especially sodium, and tetraalkyl-ammonium cations, the alkyl groups of which preferably contain 2-5 carbon atoms. In a particularly preferred class of catalysts for purposes of the present invention, the molar ratio of $SiO_2$ to $Al_2O_3$ in the latter formula is within the ratio of about 20 to 60.

The ZSM-5 zeolites in most cases have a distinguishing crystalline structure yielding an X-ray diffraction pattern determined as described in U.S. Pat. No. 2,702,886, with significant lines as indicated in Table I, wherein "s"=strong, "w" weak and "v.s."=very strong.

TABLE I

| Interplanar Spacing d(A): | Relative intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 | |
| 5.97 ± 0.1 | w. |
| 5.56 ± 0.1 | w. |
| 5.01 ± 0.1 | w. |
| 4.60 ± 0.06 | w. |
| 4.25 ± 0.06 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

The active catalyst of this type which may be utilized in the process of the present invention, is characterized as an "H-ZSM-5" zeolite and is prepared from a "ZSM-5" zeolite by replacing most, and generally at least about 80% of the cations of the latter zeolite with hydrogen ions using techniques well-known in the art.

Examples of lower acetals or ketals which may be reacted with the phenol are 1,1-dimethoxyethane, 1,1-diethoxyethane, 1,1-dimethoxypropane 2,2-dimethoxypropane, and 1,1-diethoxypropane. The preferred acetal or ketal is 1,1-dimethoxyethane which yields 2-(1'-methoxyethyl) phenol as the preferred product.

The reaction may be carried out in vapor or liquid state under a wide variety of conditions. Reaction temperatures may be employed, for example in the range of about 200° to 400° C., preferably about 240° to 320° C. The pressure is generally uncritical to the reaction and subatmospheric, atmospheric or superatmospheric pressures may be employed. In most cases, however, the pressure of the reaction will be in the range of about 1 to 20 atmospheres absolute.

Although the reaction consumes one mole of phenol per mole of lower acetal or ketal to produce a mole of 1-hydroxy-2-(1'-lower alkoxyalkyl) benzene, the actual molar ratio of phenol to lower acetal or ketal in the feed stream may be varied between wide limits, e.g. from about 100:1 to 1:100. It is preferred however that such ratio be in the range of about 1:20 to 1:1.

If the substituted benzene and lower acetal or ketal are in the vapor state at the reaction temperature, then they can be fed in undiluted state or diluted with a relatively inert carrier gas, such as nitrogen, argon, helium, and the like. Likewise, if the reactants are liquid at the reaction temperature, then they also can be used either alone or with a suitable diluent.

Water may be present in the reactant feed stream. If water is utilized its amount can range from about 0.5 mole up to about 2 moles of water per mole of phenol and, preferably, ranges from about 1 to 2 moles of water per mole of phenol feed.

Contact or residence time can also vary widely, depending upon such variables as the nature of the reactants, catalyst, reactor, temperature and pressure. Typical contact times range from a fraction of a second to more than several hours when a catalyst system other than a fixed bed is used, with preferred contact times, at least for vapor phase reactions, between about 0.5 and 20 seconds.

Typically, the catalyst is employed in a fixed bed reactor e.g. in the shape of an elongated pipe or tube where the reactants, typically in the vapor form, are passed over or through the catalyst. Other reactors, such as fluid or ebullient bed reactors, can be employed, if desired. In some instances, it is advantageous to use the catalyst in conjunction with an inert material such as glass wool to regulate the pressure drop of the reactant stream through the catalyst bed and the contact time of the reactant compounds with the catalyst particles.

The following examples are illustrative embodiments of this invention.

EXAMPLES 1 TO 4

The catalyst utilized was an H-ZSM-5 zeolite prepared by replacing with hydrogen ions all but 500 ppm based on the weight of the zeolite of the sodium ions in a sodium aluminosilicate ZSM-5 catalyst prepared in accordance with U.S. Pat. No. 3,702,886, in which the ratio of silica to alumina was about 12. Varying amounts of this catalyst in conjunction with 1.2-1.3 g of glass wool was charged to about a ¼ in. O.D. stainless steel tube, resulting in varying lengths of catalyst bed in the tubular reactor.

A feed liquid was prepared by mixing phenol and 1,1-dimethoxyethane in a 1:10 molar ratio of phenol to acetal. The vapor effluent was condensed in an ice cooled trap and collected. After four hours the liquid feed was stopped and the passage of helium carrier gas was continued for another 1½ hours to yield a product condensate.

Analysis of the product showed identifiable amounts in the various examples of 2-(1'-methoxyethyl) phenol (2-MEP), phenyl methyl ether (PhOMe), phenyl ethyl ether (PhOEt), 2-hydroxyacetophenone (2-HAP), 2-methoxyacetophenone (2-MeAP), and 4-methoxyacetophenone (4-MeAP).

Specific values for reaction conditions which varied among the examples including catalyst weight, average reaction temperature and pressure and helium flow, contact time, and the results of the product analysis are shown in Table II. Values for percent conversion of phenol were calculated by dividing the moles of total product times 10 by the moles of phenol fed. The selectivity was calculated by dividing the percent convertion to the indication compound by the percent conversion to total products.

TABLE II

| Example | 1 | 2 | 3 | 4 |
|---|---|---|---|---|
| Catalyst Weight (g) | 5.05 | 4.96 | 4.91 | 5.66 |
| Av. Reaction Temp. (°C.) | 248.8 | 298.0 | 250.8 | 295.0 |
| Av. Reaction Press. (atm) | 7.5 | 7.5 | 8.2 | 8.8 |
| Av. He Flow (ml/min.) | 282.4 | 281.0 | 274.0 | 200.4 |
| Contact Time (secs.) | 6.3 | 5.7 | 6.9 | 10.5 |
| Conv. of Phenol (%) | 34.0 | 23.0 | 20.2 | 26.4 |
| Selectivity (%) | | | | |
| 2-MEP | 21.5 | 25.0 | 58.7 | 15.0 |
| PhOMe | 1.4 | 4.0 | 0.3 | 4.4 |
| PhOEt | 65.5 | 40.0 | 20.4 | 16.0 |
| 2-HAP | — | — | 6.4 | 6.6 |
| 2-MeAP | — | — | — | 2.2 |
| 4-MeAP | — | — | — | 20.2 |
| unknowns | 11.6 | 31.0 | 14.2 | 35.6 |

The results shown in Table II indicate that in all four examples, the only 1'-methoxyethyl phenol produced in identifiable amount of the three possible isomers was the 1,2-isomer, viz. 2-(1'-methoxyethyl) phenol.

The procedures of Examples 1 to 4 could also be used to produce 2-(1'-ethoxyethyl) phenol from phenol and 1,1-diethoxyethane; 2-(methoxymethyl) phenol from phenol and 1,1-dimethoxymethane; and 2-(2'-methoxy-2'-propyl) phenol from phenol and 2,2-dimethoxypropane.

I claim:

1. A process for the production of a 1-hydroxy-2-(1'-lower alkoxyalkyl) benzene by reaction of phenol with a lower acetal or ketal comprising contacting a feed stream comprising said phenol and lower acetal or ketal at an elevated temperature with a protonated ZSM-5 zeolite as catalyst.

2. The process of claim 1 wherein said ZSM-5 zeolite has the formula:

$$0.9 \pm 0.2 M_{2/n}O:W_2O_3:5-100YO_2 \cdot zH_2O$$

wherein M is a cation, n is the valence of said cation, W is selected from the group consisting of aluminum and gallium, Y is selected from the group consisting of silicon and germanium, and z is from 0 to 40, and in which at least about 80% of the cations are replaced with hydrogen ions.

3. The process of claim 2 wherein said ZSM-5 zeolite has an X-ray diffraction pattern with lines as shown in Table I of the specification.

4. The process of claim 3 where said catalyst has the formula:

$$0.9 \pm 0.2 M_{2/n}O:Al_2O_3:5-100SiO_2 \cdot zH_2O$$

and M is selected from the group consisting of alkali metal cations and tetraalkylammonium cations, the alkyl groups of which contain 2–5 carbon atoms.

5. The process of claim 4 wherein the ratio of $SiO_2$ to $Al_2O_3$ in said catalyst is in the range of about 10 to 30.

6. The process of claim 1 wherein said reaction proceeds in accordance with the following equation:

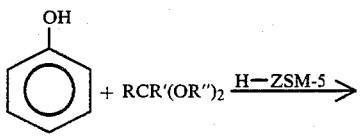

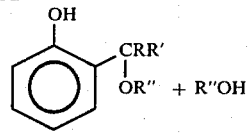

where R and R' are each hydrogen or lower alkyl containing 1 to 3 carbon atoms, and R'' is lower alkyl containing 1 to 3 carbon atoms and R and R', if lower alkyl, and R'', may be the same or different.

7. The process of claim 6 wherein said ZSM-5 zeolite has the formula:

$$0.9 \pm 0.2 M_{2/n}O:W_2O_3:5-100YO_2 \cdot zH_2O$$

wherein M is a cation, n is the valance of said cation, W is selected from the group consisting of aluminum and gallium, Y is selected from the group consisting of silicon and germanium, and z is from 0 to 40, and in which at least about 80% of the cations are replaced with hydrogen ions.

8. The process of claim 7 wherein said ZSM-5 zeolite has an X-ray diffraction pattern with lines as shown in Table I of the specification.

9. The process of claim 8 where said catalyst has the formula:

$$0.9 \pm 0.2 M_{2/n}O:Al_2O_3:5-100SiO_2 \cdot zH_2O$$

and M is selected from the group consisting of alkali metal cations and tetraalkylammonium cations, the alkyl groups of which contain 2–5 carbon atoms.

10. The process of claim 9 wherein the ratio of $SiO_2$ to $Al_2O_3$ in said catalyst is in the range of about 10 to 30.

11. The process of claim 6 wherein said acetal or ketal is 1,1-dimethoxyethane.

12. The process of claim 6 wherein said reaction occurs in the vapor phase and said elevated temperature is in the range of about 200° to 400° C.

13. The process of claim 6 wherein said temperature is in the range of about 240° to 320° C.

14. The process of claim 6 wherein said catalyst is in the form of a fixed bed and said feed stream into said bed also contains an inert carrier gas.

15. The process of claim 6 wherein said reaction occurs in the vapor phase and the contact time of reactants with catalyst is from about 0.5 to 20 seconds.

16. The process of claim 6 wherein the molar ratio of phenol to lower acetal or ketal in the feed stream is in the range of about 1:20 to 1:1.

* * * * *